(12) United States Patent
Amis

(10) Patent No.: US 6,755,834 B2
(45) Date of Patent: Jun. 29, 2004

(54) CRANIAL FLAP FIXATION DEVICE

(75) Inventor: James Peter Amis, Carlsbad, CA (US)

(73) Assignee: Medtronic, Inc., Minneapolis, MN (US)

( * ) Notice: Subject to any disclaimer, the term of this patent is extended or adjusted under 35 U.S.C. 154(b) by 29 days.

(21) Appl. No.: 09/954,611

(22) Filed: Sep. 17, 2001

(65) Prior Publication Data

US 2002/0062128 A1 May 23, 2002

Related U.S. Application Data

(60) Provisional application No. 60/232,689, filed on Sep. 15, 2000.

(51) Int. Cl.$^7$ ............................................... A61B 17/56
(52) U.S. Cl. ............................. 606/72; 606/73; 606/104
(58) Field of Search ........................... 606/72, 73, 77, 606/69, 104; 623/17.19

(56) References Cited

U.S. PATENT DOCUMENTS

| | | | |
|---|---|---|---|
| 5,707,373 A | * | 1/1998 | Sevrain et al. ................. 606/72 |
| 5,800,436 A | | 9/1998 | Lerch |
| 6,068,631 A | | 5/2000 | Lerch |
| 6,146,384 A | | 11/2000 | Lee et al. |
| 6,179,839 B1 | * | 1/2001 | Weiss et al. ................... 606/77 |
| 6,258,091 B1 | * | 7/2001 | Sevrain et al. ................. 606/72 |
| 6,270,500 B1 | | 8/2001 | Lerch |
| 6,328,743 B2 | | 12/2001 | Lerch |
| 6,379,363 B1 | * | 4/2002 | Herrington et al. ............ 606/72 |
| 2002/0016593 A1 | * | 2/2002 | Hearn et al. ................... 606/72 |

* cited by examiner

Primary Examiner—David O. Reip
(74) Attorney, Agent, or Firm—Shumaker & Sieffert, P.A.

(57) ABSTRACT

A cranial flap fixation device utilizing a piece design comprising an inner member and an outer member. The inner member includes a head and a shaft and the outer member comprises a nut for securing onto the shaft. A driving tool may be engaged with the inner member for secure engagement with the outer member. The present invention is also a cranial flap fixation system comprising three pieces, a nut, a bolt and a lock washer. The bolt having a threaded portion head for receipt into the nut and lock washer assembly, and the bolt also having an extra wide head portion for secure engagement inside the patient's cranium. The bolt is designed for use with a variety of bone structures since it is designed having an adjustable length so that the surgeon can cut the bolt after tightening onto the nut and lock washer assembly. A driving tool may be utilized to secure the cranial flap fixation system.

40 Claims, 11 Drawing Sheets

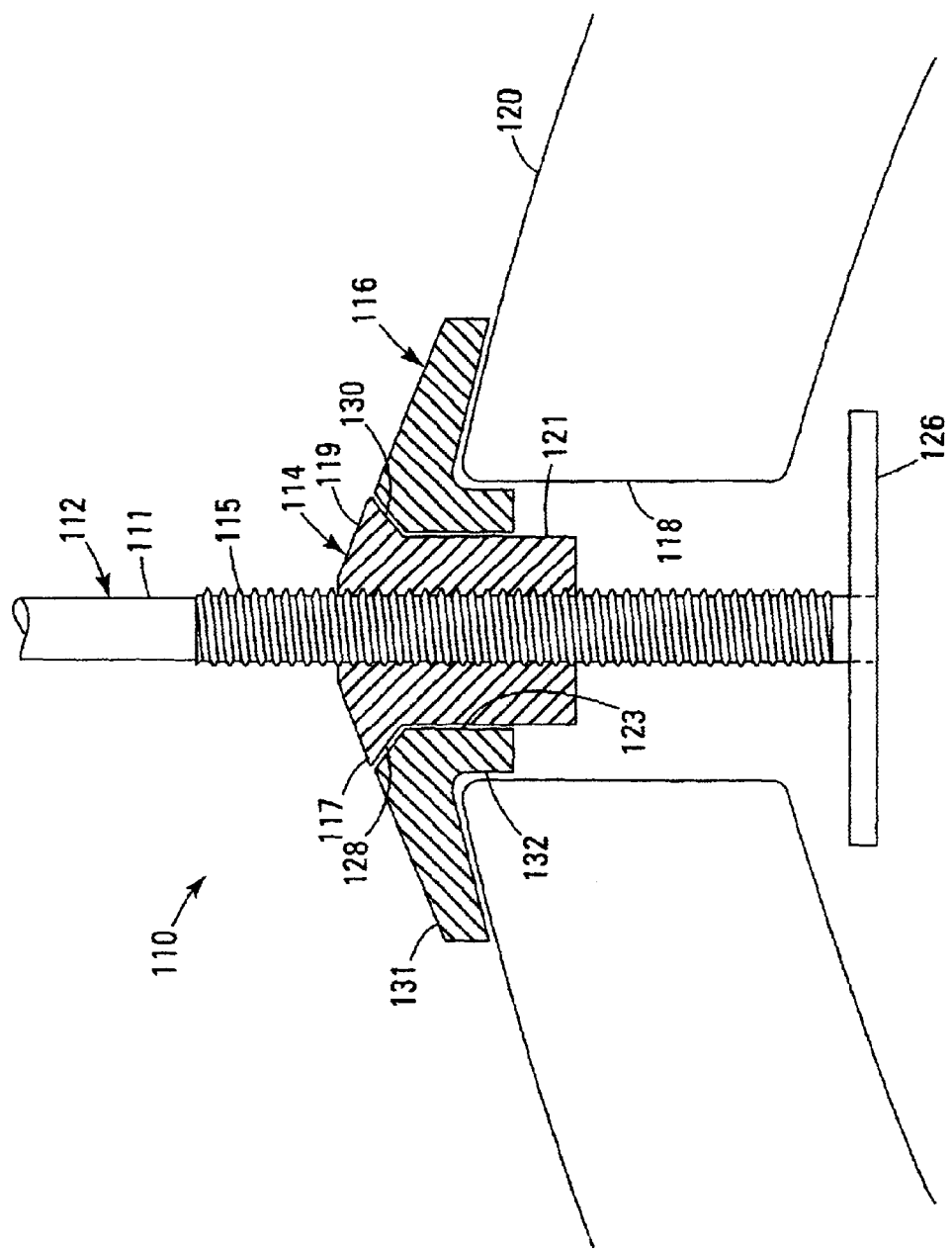

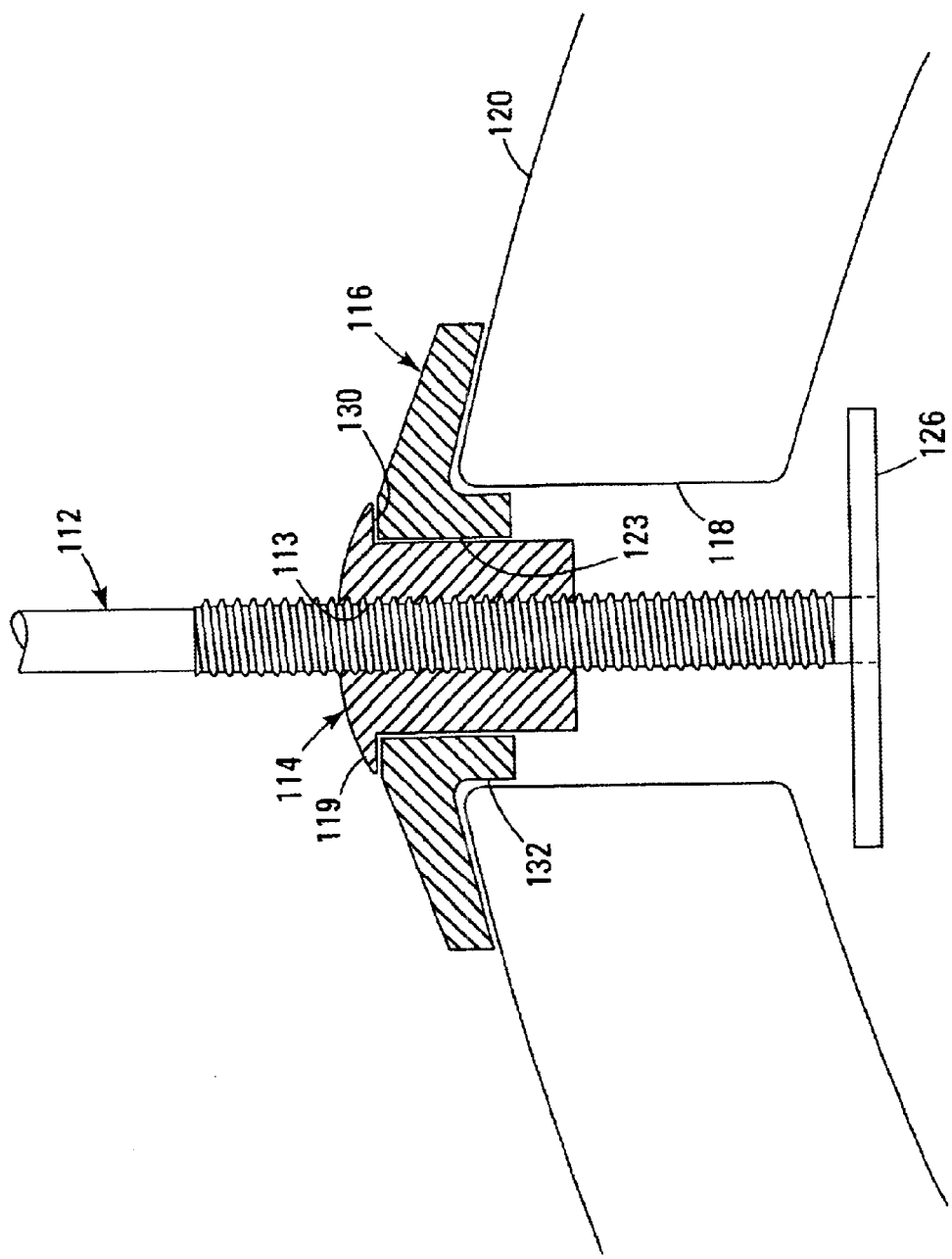

CRANIAL FLAP FIXATION DEVICE

BACKGROUND OF THE INVENTION

1. Field of the Invention

The present invention relates generally to a fastener for securing a bone flap to surrounding bone and, more particularly, to a fastener for securing a bone flap to the cranium.

2. Description of Related Art

A craniotomy is a procedure wherein a portion of the cranial vault is surgically removed to provide access by the surgeon to the inside of the head and brain. Generally, to perform the craniotomy several burr holes are drilled through the skull and then the holes are connected using an osteotomy saw to cut the skull along a line of separation connecting the adjoining burr holes. Typically, the number and position of the burr holes will vary depending on the size and shape of the bone flap to be removed. For example, if one desired to remove a triangularly shaped bone flap then it may be practical to drill three burr holes to form a triangle and then use the osteotomy saw to connect the corners of the triangle for removal of the bone flap. Once the cuts have been made, the bone flap can be lifted from the underlying dura matter to expose the brain or other portion of the head. The bone flap may be removed entirely or folded back in a flap along one uncut or partially cut edge.

Once the operation has been completed, the surgeon will typically replace the bone flap to protect the underlying brain. An approach for reattaching the bone flap to the cranium may comprise drilling holes into the bone flap and surrounding cranium near the osteotomy and, subsequently, using stainless steel wire or silk sutures to reattach the bone flap to the holes. However, this procedure may be time consuming in that numerous holes must be drilled and, additionally, the drilling procedure may increases a risk of infection. At the same time, sutures have been known to become unstable and even to break which can also lead to dangerous movements of the bone flap against the brain. Furthermore, suture materials may leave irregularities in the skin surface and may fail to align the bone plate in a substantially planar fashion relative to the surface of the cranium.

Bone flap fastening devices that do not utilize sutures have been known in the prior art. One such device is described in U.S. Pat. No. 5,707,373 to Sevrain et al. This patent discloses the use of two interlocking pieces that form a cap and base structure to attach the bone flap to the cranium. The cap and base structure described therein extends from the burr hole over the cranium to secure the bone flap. Such a device may still be prone to movement of the fixation device such as "backing out" or loosening of the cap and the base. Accordingly, the need for a relatively safe, secure and easy to place cranium fixation device that is also aesthetically pleasing remains.

SUMMARY OF THE INVENTION

The cranial flap fixation device of the present invention utilizes a two or three piece design for attachment of a bone flap or bone plate to a cranium. The two piece design comprises in one embodiment an inner member and an outer member. The inner member comprises a head and a shaft and the outer member comprises a nut for attachment onto the shaft. A driving tool may be engaged with the outer member for manipulation of the outer member to thereby provide a secure engagement of the outer member with the inner member.

In a further embodiment, the inner member comprises a bolt, and the outer member comprises a nut and a lock washer. When utilized, the lock washer of the present invention is engaged and biased between the nut and an edge of the burr hole. The nut imparts a downward force onto a generally radially-inwardly located portion of the lock washer, and the edge of the burr hole imparts an upward force onto a radially intermediate portion of the lock washer. In accordance with one aspect of the present invention, the lock washer is constructed of a plastic or other semi-rigid material. The downward and upward forces exerted by the nut and the burr hole edge, respectively, place a bind on the lock washer and help to prevent the lock washer and nut from loosening or backing out. The fixation device of the present invention can further utilize a driving tool for engagement with the nut and for optional engagement with the lock washer. The fixation device of the present invention may further reduce a potential of over torquing the nut, thereby attenuating a possibility that the nut or bolt will be stripped or otherwise damaged.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 11 is a cross-sectional view of a three piece embodiment of the cranial flap fixation device of the present invention;

FIG. 14 is a cross-sectional view of yet another construction of the three piece embodiment of the cranial flap fixation device of the present invention.

DETAILED DESCRIPTION OF THE PRESENTLY PREFERRED EMBODIMENTS

Figure 1:
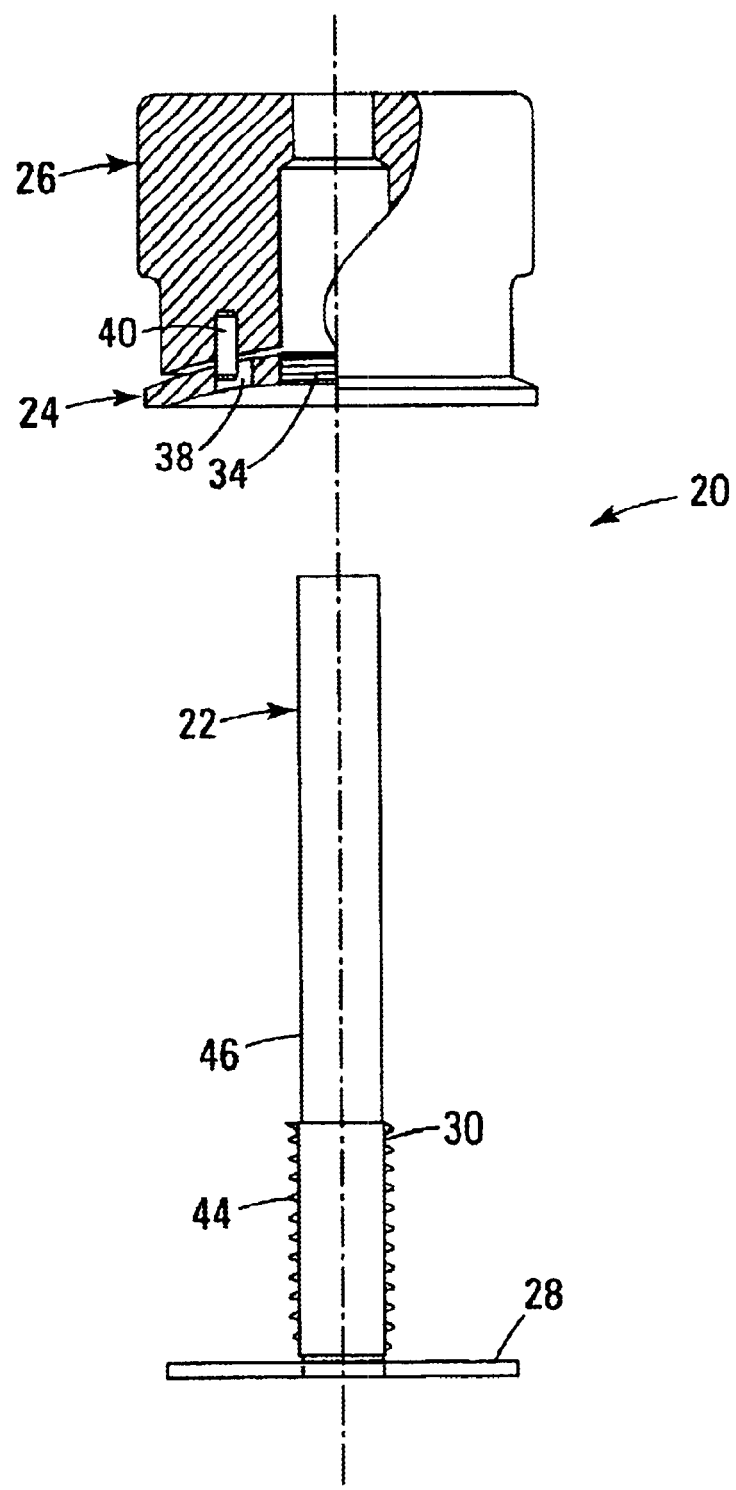
FIG. 1 is a side elevation view of the two piece cranial flap fixation device of the present invention.

With reference to FIG. 1, the fixation system 20 of the present invention comprises an inner member 22, an outer member 24, and a driving tool 26 for engagement with the outer member 24. The inner member 22 comprises a head 28 and a shaft 30, and the outer member 24 preferably comprises a nut for being secured onto the shaft 30.

Figure 2A:
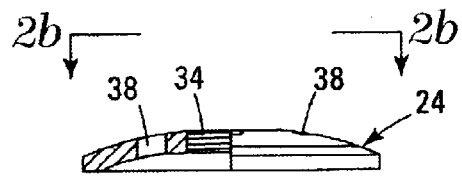
FIG. 2a is a partial cross-sectional view of the outer member of the cranial flap fixation device of the present invention.
Figure 2B:
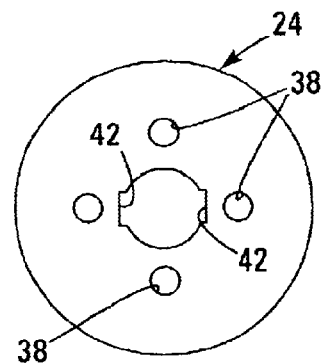
FIG. 2b is a top planar view of the outer member of the cranial flap fixation device of the present invention.
Figure 3A:
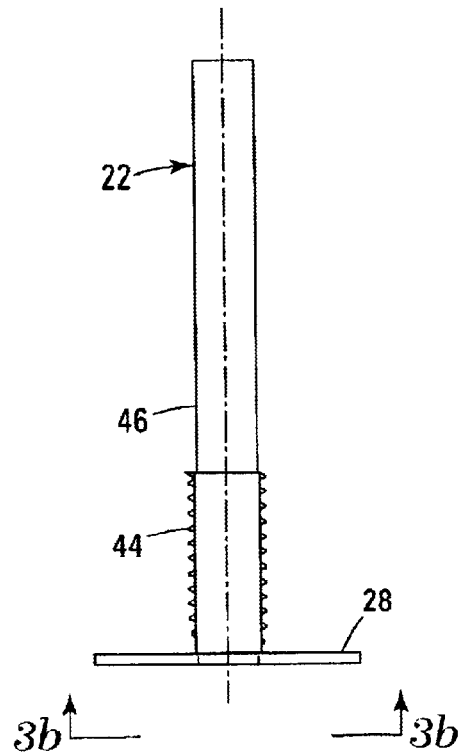
FIG. 3a is a partial cross-sectional view of the inner member of the cranial flap fixation device of the present invention.
Figure 3B:
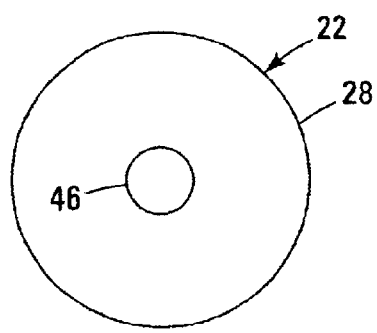
FIG. 3b is top planar view of an outer member of the cranial flap fixation device of the present invention.
Figures 4A, 4B:
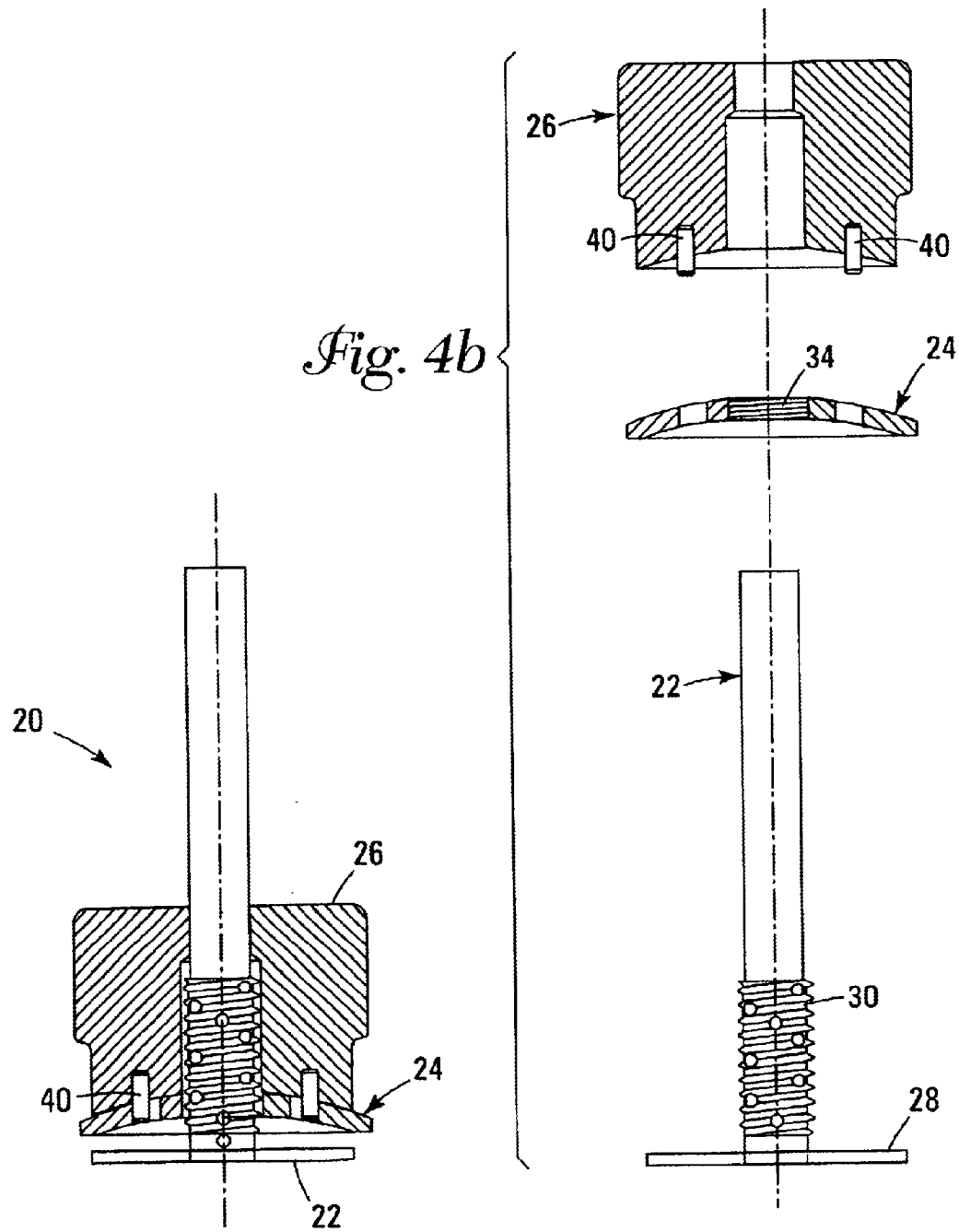
FIG. 4a is a cross-sectional view of the two piece cranial flap fixation device with a driving tool in accordance with the present invention.
FIG. 4b is another cross-sectional view of the cranial flap fixation device including a driving tool in accordance with the present invention.

FIG. 2a illustrates a partial cross-sectional view of the outer member 24, and FIG. 2b illustrates a top planar view of the outer member 24. FIG. 3a illustrates a side-elevation view of the inner member 22, and FIG. 3b illustrates a top planar view of the inner member 22. FIG. 4a shows the outer member 24 and the driving tool 26 secured onto the inner member 22, and FIG. 4b is an exploded view of the elements of FIG. 4a.

The outer member 24 comprises a threaded aperture 34 for accommodating the shaft 30 of the inner member 22, and further comprises at least one additional aperture or notch for accommodating the driving tool 26. In the presently preferred embodiment, the aperture or notch 36 comprises four apertures 38 disposed in the outer member 24, and the driving tool 26 comprises four mating protrusions 40 for fitting into the four apertures 38 to thereby facilitate application of torque from the driving tool 26 onto the outer member 24. Moreover, two notches 42 (FIG. 2b) are provided on the threaded aperture 34 for facilitating the application of torque to the outer member 24 by one or more tools when one or more of the additional apertures or notches 38 is/are covered or obstructed (e.g., with surrounding tissue). In a modified embodiment, this driving tool 26 may be constructed with corresponding structure to fit into the notches for application of torque. In other embodiments, either apertures 38 or notches 42, or both, may be omitted, and other structures such as a single or two perpendicular slots for accommodating a flat-headed or Phillips head screwdriver may be constructed.

As shown in FIG. 1, the shaft 30 preferably comprises a threaded portion 44 and an extended portion 46. In the presently preferred embodiment, the threaded portion 44 is constructed to accommodate internal threads of the outer member 24, and the extended portion 46 does not comprise threads. In modified embodiments, the threads of the threaded portion 44 may be disposed on part or all of the extended portion 46 as well.

The fixation system 20 preferably is provided in sterile packaging, and the outer member 24 and driving tool 26 are preferably packaged in a pre-assembled configuration as shown in FIG. 1. In modified embodiments, the outer member 24 and driving tool 26 are packaged separately.

Figure 7A:
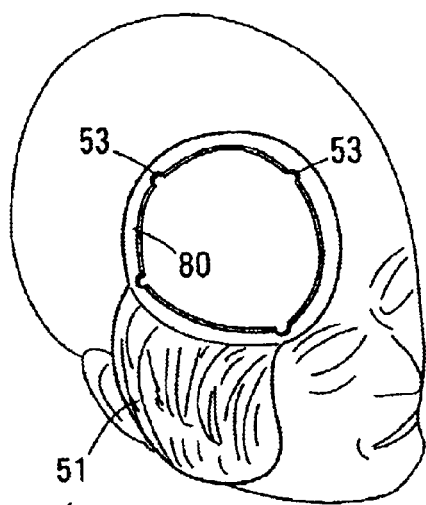
FIG. 7a is a perspective view of the preparatory procedure of the surgical method of the present invention.
Figure 7B:
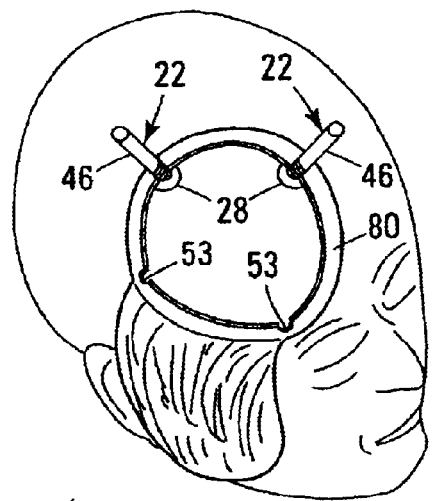
FIG. 7b is a perspective view of the secondary procedure of the surgical method of the present invention.
Figure 7C:
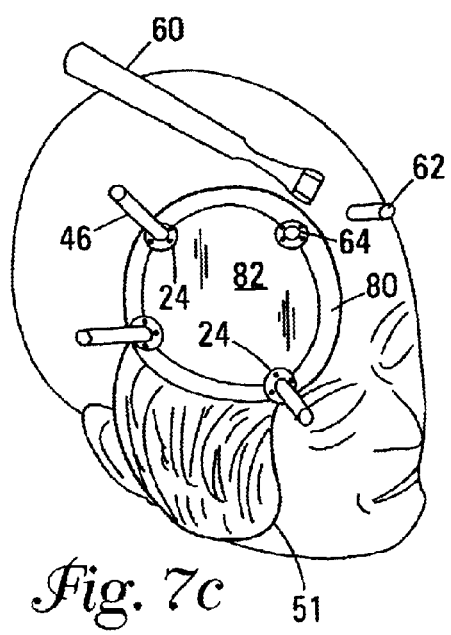
FIG. 7c is a perspective view of the final procedure of the surgical method of the present invention.

The inner member 22 and the outer member 24 are preferably screwed together to provide fixation between two adjacent bone sections. In a craniotomy procedure, for example, the bone sections comprise the in-tact cranium and the craniotomy bone flap. In one embodiment, the fixation system 20 can be constructed to fit within and overlap around the perimeter of the burr hole, which is typically between 8 mm and 17 mm in diameter. FIGS. 7a, 7b and 7c illustrate a craniotomy procedure, wherein a bone flap is removed and then replaced with the fixation system of the present invention. In FIG. 7a, a flap of tissue 51 is first removed. A plurality of burr holes 53 are next placed within the cranium. Subsequently, the burr holes are connected with a cutting tool to form a kerf surrounding the bone flap. The bone flap is then removed. As shown in FIG. 7b, a plurality of inner members 22 are placed within the burr holes 53. A surgeon can grip each inner member 22 by its extended portion 46 for positioning within a burr hole 53. The head 28 will rest on the dura matter of the brain. After positioning, each inner member 22 can be held by a hand of the surgeon or an assistant, or may be frictionally held by a snug fit between the head 28 and both the dura matter and the cranium and between the shaft 30 and the cranium bone surrounding the burr hole 53, and/or by other means.

In accordance with one aspect of the present invention, one or more of the outer members 24 may be secured onto the threaded portions 44 of the inner members 22 for positioning and holding during the procedure. For example, the two inner members 22 shown in FIG. 7b may be secured within two burr holes 53 of the cranium, with two outer members 24, while other inner members 22 are inserted and positioned within the remaining burr holes. The other inner members 22 are then held in place by a hand of a surgeon while the bone flap is placed back onto the cranium over the heads 28 of the inner members. After the bone flap is placed, the outer members 24 are secured onto the threaded shafts 44 of the inner members 22 that do not already have outer members 24 secured thereon.

In the illustrated embodiment of FIG. 7b, the two inner members 22 are held in place by the hand of a surgeon while the remaining inner members 22 are inserted and positioned. Then, with all of the inner members being positioned or held by a surgeon or surgeons, the bone flap is placed back onto the cranium. The outer sides (i.e., the sides furthest away from the bone flap) of the extended portions 46 can be held by the surgeon or surgeons so that the hands of the surgeon (s) holding the inner members 22 do not interfere with the placement of the bone flap back onto the cranium. One or more of the extended portions 46 may be oriented to point slightly away from the bone flap during positioning of the bone flap, to facilitate insertion of the bone flap onto the cranium.

The hands of the surgeon(s) holding the inner members 22 can help to guide the bone flap back into position while also maintaining the positioning of the inner members 22. In addition and/or as an alternative to the hands of the surgeon (s) helping to guide and place the bone flap back onto the cranium, one or more of the shafts 30 of the inner portions 22 may be used as guides in aiding the alignment and positioning of the bone flap back onto the cranium.

As just one application, in the above example wherein one or more of the outer members 24 are secured onto the shafts 30 before placement of the bone flap back onto the cranium, the surgeon placing the bone flap may place the bone flap into contact with one or more shafts 30 that are fastened with an outer member 24, for assistance in the positioning and alignment of the bone flap during placement thereof back onto the cranium. In embodiments wherein one or more of the shafts are used to assist in the placement of the bone flap back onto the cranium, it is preferred but not required to configure the extended portions 46 of the shafts 30 to be relatively smooth. The inner members 22 are thus held while the bone flap is placed back onto the cranium over the heads 28 of the inner members. After the bone flap is placed, the outer members 24 are secured onto the threaded shafts 44 of the inner members 22.

As shown in FIG. 7c, after an outer member 24 is secured onto a corresponding inner member 22, the high-temperature wire of a cutting tool 60 is used to cut the protruding portion 62 of the shaft 30. All of the protruding portions 62 are removed before the flap 51 is replaced. The protruding portion 62 will typically comprise the extended portion 46 and part of the threaded portion 44 of the shaft 30. Each protruding portion 62 is preferably cut so that the remaining part of the shaft 30 is substantially flush with, or slightly protruding from, the top surface of the outer member 24. The termination (or stub) of the shaft 30 at the surface of the outer member 24 is shown at 64 in FIG. 7c.

Figure 9A:
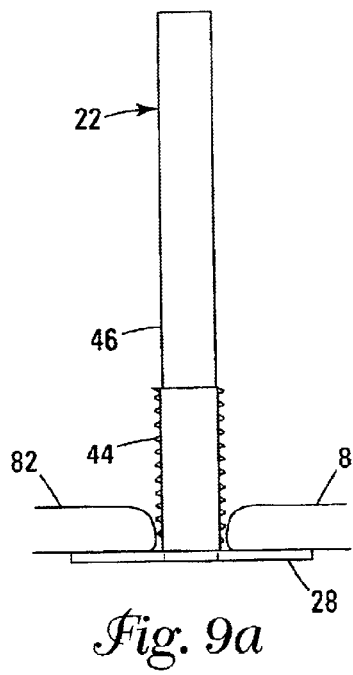
FIGS. 9a–9c are side views corresponding to the surgical method of FIGS. 7a–7c.
Figure 9B:
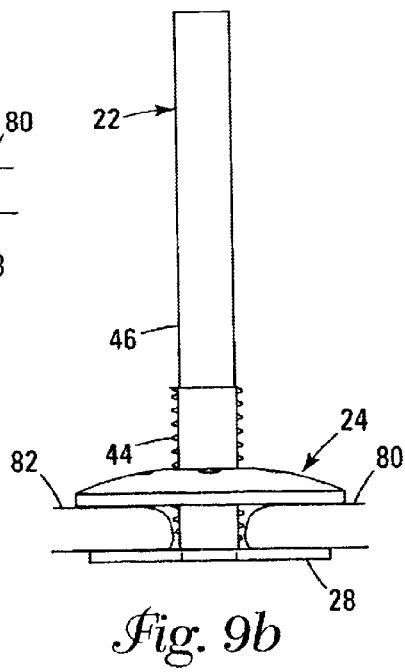
Figure 9C:
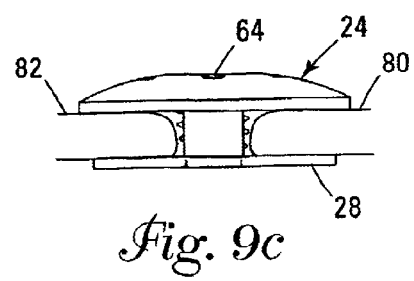

FIGS. 9a, 9b and 9c illustrate cross-sectional views of the fixation system 20 shown in FIGS. 7a, 7b and 7c. In FIG. 9a the inner member 22 is positioned between the cranium 80 and the bone flap 82, and in FIG. 9b the outer member 24 is secured onto the inner member 22 to fixate the bone flap 82 relative to the cranium 80. The protruding portion 62 (FIG. 7c) is removed in FIG. 9c so that the termination of the shaft 30 is substantially flush with the top surface of the outer member 24. FIG. 9c shows the termination of the shaft 30 in the form of a stub 64 slightly protruding from the top surface of the outer member 24. When the outer members 24 are secured to the inner members 22, the heads 28 of the inner members 22 will align and hold the bone flap at the proper elevation relative to the surrounding cranium.

The passing of the high-temperature wire through the threaded portion 44 will tend to distort the threads of the threaded portion 44, thus serving to lock the outer member 24 on the threaded portion 44 of the inner member 22. Should the surgeon desire to remove the outer member 24, the outer member 24 may be counter-rotated off of the threaded portion 44 using the driving tool 26. Alternatively, if for example, body tissue or fluids have occluded one or more of the apertures 38 on the outer member 24, then the notches 42 on the outer member 24 may be used for removal and/or subsequent reinsertion of the outer member 24. The removal of the outer member 24 will re-thread the stub of the shaft 30 for subsequent re-insertion of the outer member 24 thereon. Once the outer member or members 24 has been removed, however, the surgeon may choose to replace the cut inner member or members 22 with a new one or ones.

In another embodiment, the fixation system is constructed to fit within and overlap onto the adjacent bone sections of the kerf, which can be, for example, approximately 1.5 mm in width. The diameters of the head 28 and the outer member 24 will be commensurately constructed to have larger diameters for burr-hole fixation and relatively smaller diameters for kerf fixation. The width of the shaft 30 and threaded aperture 34 may also be reduced to accommodate the smaller spacing between the cranium 80 and bone flap 82 formed by the kerf.

Figure 8A:
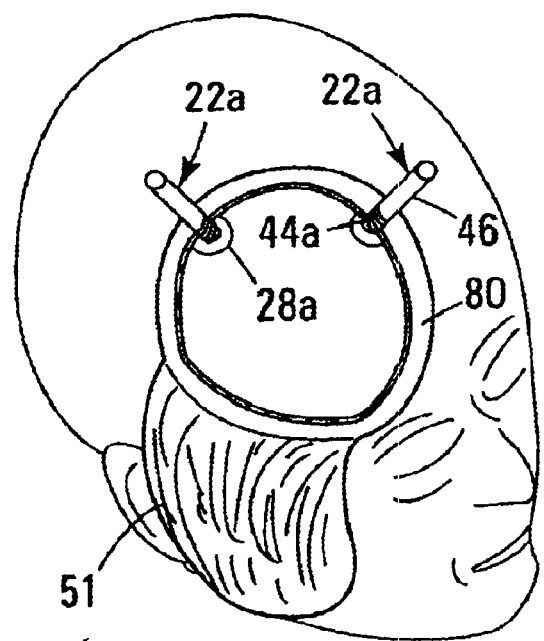
FIG. 8a is a perspective view of the secondary procedure of a similar surgical method of the present invention.
Figure 8B:
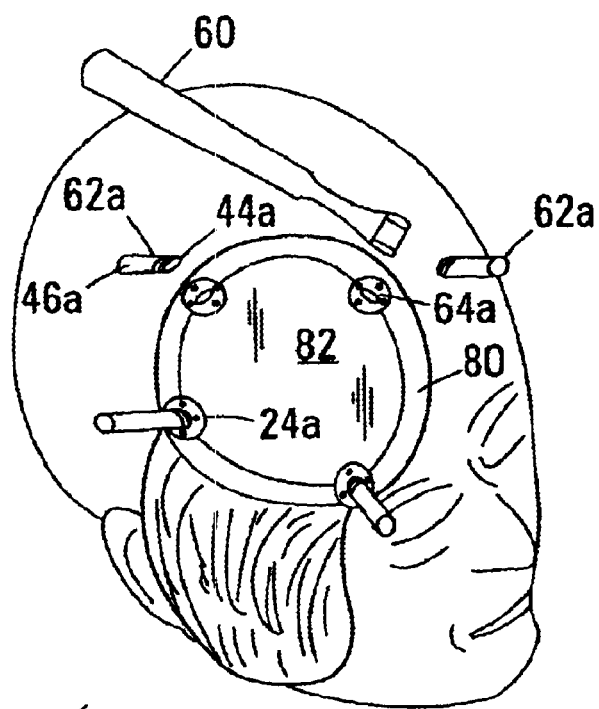
FIG. 8b is a perspective view of the final procedure of the similar surgical method of the present invention.
Figure 10A:
FIGS. 10a–10d are top views of several embodiments of the shaft 46 of FIGS. 9a–9c.
Figure 10B:
Figure 10C:
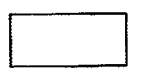
Figure 10D:
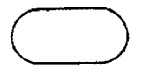

FIGS. 8a and 8b illustrate a craniotomy procedure which does not use burr holes for defining and removing the bone flap. In FIG. 8a, the flap of tissue 51 is removed, and a cutting tool is used to form a kerf surrounding the bone flap. The bone flap is then removed. A plurality of inner members 22a are then placed within the kerf in a manner similar to that described above with reference to FIGS. 7a, 7b and 7c. In the illustrated embodiment of FIG. 8a, the two inner members 22a are held in place by for example the hand of a surgeon while the remaining inner members 22a are inserted and positioned. As with the embodiment of FIG. 7a, 7b and 7c, the surgeon may select the number of inner and outer members 22, 24 to be used in accordance with preference and the application at hand. With the inner members being held by for example a surgeon or surgeons, (and/or by one or more outer members 24) the bone flap is placed back onto the cranium. The inner members 22a are thus held while the bone flap is placed back onto the cranium over the heads 28a of the inner members. After the bone flap is placed, an appropriate number of outer members 24a are secured onto the threaded shafts 44a of the inner members 22a.

As shown in FIG. 8b, after each outer member 24a is secured onto a corresponding inner member 22a, a high-temperature wire of a cutting tool 60 is used to cut the protruding portion 62a of the shaft. FIG. 8b shows all of the outer members 24 secured, and two protruding portions 62a removed. In the illustrated embodiment, the flap 51 is replaced and all of the protruding portions 62a are removed. The protruding portion 62a will typically comprise the extended portion 46a and part of the threaded portion 44a of the shaft. The protruding portion 62a is preferably cut so that the remaining part of the shaft is substantially flush with, or slightly protruding from, the top surface of the outer member 24a. The termination (or stub) of the shaft at the surface of the outer member 24a is shown at 64a in FIG. 8b. The passing of the high-temperature wire through the threaded portion 44a will tend to distort the threads of the threaded portion 44a at the cut, thus helping to lock the outer member 24a on the threaded portion 44a of the inner member 22a.

Should the surgeon desire to remove the outer member 22a, the outer member 22a may be counter-rotated off of the threaded portion 44a using the driving tool 26. Alternatively, if body tissue or fluids have occluded one or more of the apertures 38 on the outer member 24a, then two inner notches (not shown, but similar to 42 in FIG. 2b) on the outer member 24a may be used for removal and/or subsequent reinsertion thereof. The removal of the outer member 24a will re-thread the stub of the shaft for subsequent re-insertion of the outer member 24a thereon. Once the outer member 24a has been removed, the surgeon may choose to replace the cut inner member 22a with a new one.

In an embodiment, wherein the fixation system is not used in a burr hole (such as, for example, wherein it is used in the kerf), the shaft may comprise an elliptical or rectangular cross section. In such an embodiment, the shaft has a reduced thickness along a first axis that is transverse to the longitudinal axis of the shaft, and the shaft has a relatively enhanced thickness along a second axis that is normal to the first axis and transverse to the longitudinal axis of the shaft. Thus, if the longitudinal axis of the shaft is z, then the diameter of the shaft in the x direction, for example, would be greater than the diameter of the shaft in the y direction. In an embodiment wherein the shaft has a rectangular cross section, the two opposing sides furthest apart will have the threads disposed thereon. In another embodiment, the shaft has a square cross-section with all four sides and/or corners threaded. FIGS. 8a and 8b illustrates a rectangular cross-sectioned shaft configured to fit within a kerf. FIGS. 10a, 10b, 10c and 10d illustrate several exemplary cross-sections of the shaft for fitting within the kerf.

Figure 5:
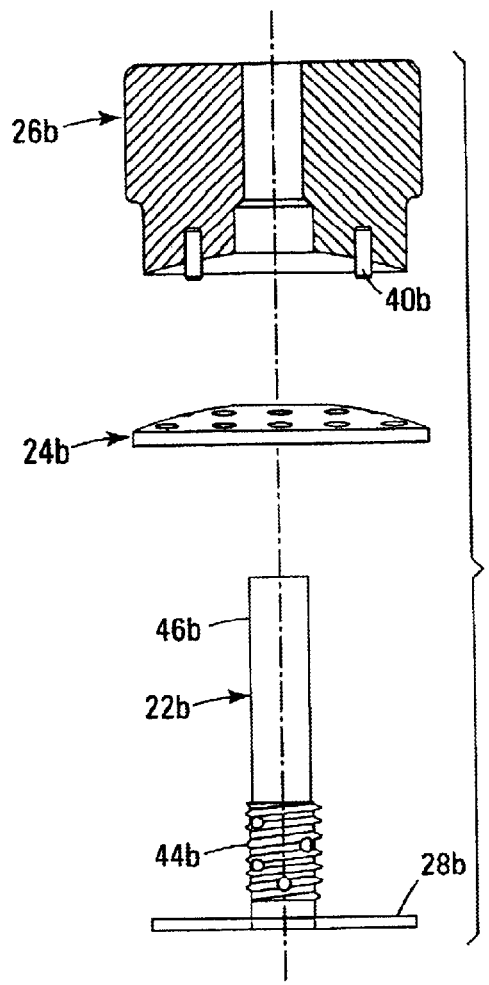
FIG. 5 is a cross-sectional view of another embodiment of the cranial flap fixation device of the present invention.

In a modified embodiment, the inner and outer members are provided with cross-drilled holes for facilitating ingrowth of new bone therethrough. FIG. 5 shows an exploded view of the outer member 24b, the driving tool 26b, and the inner member 22b, in accordance with a modified, perforated embodiment. FIG. 6 illustrates a top planar view of the outer member 24c in accordance with an implementation of the modified, perforated embodiment, in which the uneven periphery of the outer member 24c can facilitate positioning, insertion, and removal of the outer member 24c. The perforations can be added in various sizes, shapes and distributions, at different locations on the device or homogeneously, to both facilitate healing and control the rate of biodegradation of the various parts and portions of the fixation device or system. Moreover, substances may be implanted within various parts and portions of the fixation device, with or without the perforations.

In one preferred embodiment, one or more chambers are disposed within the fixation device. For example, a chamber may be disposed within the shaft of the inner member 22, along with pores connecting the chamber to the outer surface of the inner member 22.

Medicinal or other substances can be placed within the chamber for delivery to the surrounding tissue after implantation of the inner member. The pores may be placed in only portions of the inner member 22 for directional delivery of the substance or substances, and carriers may be used with the substances to further control the timing and direction of delivery of the substances to one or more surrounding areas of the inner member 22. The rate of biodegradation of one or more components of the fixation device may further be controlled. For example, the fixation device may be configured to biodegrade in a relatively short period, or on the other extreme, may be configured to remain in the body permanently. Although a resorbable fixation device is presently preferred, a non-resorbable fixation device in accordance with the present invention may be configured of, for example, a non-resorbable plastic or titanium. In the titanium embodiment, the protruding portion 62 will likely need to be clipped or sawed. PCT Application Number PCT/US00/29739, the entire contents of which are expressly incorporated herein by reference, discloses implantable substance delivery devices having chambers and pores and methods which can be used with the fixation device of the present invention. In one embodiment, the chamber may extend along a part or the entire longitudinal axis of the inner member 22 for facilitating delivery of substances therethrough at a later date after the fixation device has been implanted.

In an embodiment wherein the channel extends through the entire inner member 22, the longitudinal chamber or lumen may be configured to accommodate an intra-cranial pressure monitoring device. The lumen may also be used for delivering other substances, such as chemotherapy substances, through pores in the inner member and/or via insertion of a syringe through the lumen. A cap can be placed over the outer member 24, or a portion of the threaded portion 44 of the inner member can be left in-tact to extend above the outer member 24 for accommodating a plug or screw-on cap. The plug or cap may comprise a membrane which can be punctured by a needle for delivery of substances. The pressure monitoring device may be designed to be threaded onto the protruding threaded portion 44 of the inner member.

Figure 6A:
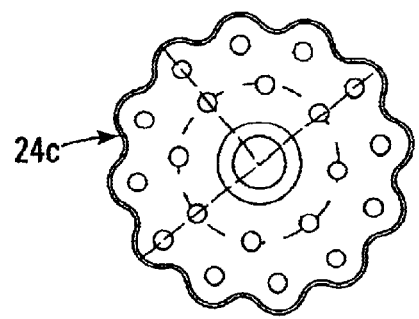
FIG. 6a is a top view of the outer member of the cranial flap fixation device shown in FIG. 5.
Figure 6B:
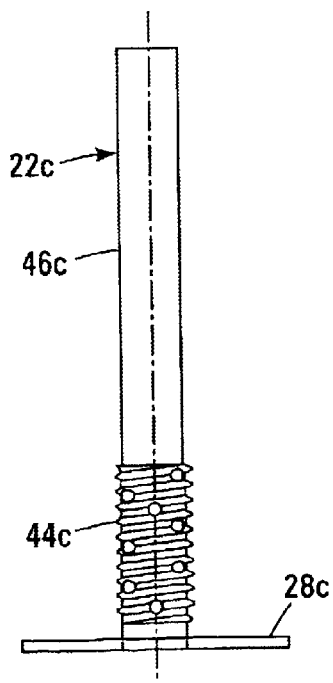
FIG. 6b is a side elevation view of the inner member of the cranial flap fixation device shown in FIG. 5.

FIGS. 6a and 6b show side elevation views of the inner member 22c and the outer member 24c. It is noted that in the illustrated embodiment of FIG. 5, the diameters of the threaded portion 44b and the extended portion 46b of the inner member 22b are not the same. This embodiment would provide greater strength to the threaded portion 44b, and conserve materials in connection with the extended portion 46b at least a portion of which is designed to be removed upon implantation of the fixation device. Although cross-drilled holes are presently preferred, any other structure or process for removing portions of the inner member (or exposing more surface thereof) and/or the outer member may be implemented. Portions of different sizes and shapes may be removed from surface disturbances or abrasions, to apertures extending all of the way through the inner member and/or outer member.

In accordance with a method of the present invention, the fixation system is used as a craniotomy bone-flap fixation system. The method utilizes the existing burr hole and osteotomy cut and does not use additional screws or tacks. A surgeon can thus fixate the craniotomy bone flap without additional drilling. The method comprises a step of the surgeon placing the head 28 of an inner member 22 inside the cranium so that the shaft 30 of the inner member is within or adjacent to the burr hole and the head 28 of the inner member is positioned to contact an inner surface of the cranium. The surgeon can then place the head 28 of a second inner member 22 inside the cranium so that the shaft 30 of the second inner member is within or adjacent to a second burr hole and the head 28 of the inner member is positioned to contact the inner surface of the cranium. Additional inner members may be similarly positioned.

The inner members 22 are positioned and held in place by, for example, the surgeon holding the shafts 30. Once the inner members 22 are positioned, they are maintained in their positions while the bone flap is placed back onto the cranium. The bone flap is placed back onto the cranium so that portions of the inner surface of the bone flap contact portions of the heads 28 of the inner portions. The heads 28 of the inner members 22 help to properly position the bone flap and hold the bone flap flush with the surrounding cranium.

The outer members 24 are then placed over the respective extended portions 46 of the inner members 22, and moved along the extended portions 46 toward the threaded portions 44. Once an outer member 24 has contacted a threaded portion 44, the surgeon will rotate the outer member 24 to advance the internal threads of the outer member 24 along the threads of the threaded portion 44. While rotating the outer member, the surgeon can grip and hold the extended portion 46 to maintain proper positioning thereof and to prevent rotation of the inner member 22 as the outer member 24 is rotated thereon. Each outer member 24 is rotated further and further onto a corresponding threaded portion 44, until the bone flap and adjacent cranium bone are both sandwiched between the head 28 of the inner member and the outer member 24.

In the presently preferred embodiment, the fixation system 20 comprises a resorbable material, such as a resorbable copolymer of 70:30 poly (L,DL) lactate. Other plastics and materials may be used in modified embodiments. The extended portion 46 of each inner member 22, along with a length of the threaded portion 44, preferably extends above the outer member 24 when the outer member is threaded onto the threaded portion 44 to hold the bone flap. After the outer members 24 are tightened onto the inner members 22, the lengths of the inner members 22 (i.e., extending portions and partial lengths of threaded portions) protruding above the outer members can be cut and removed. In the presently preferred embodiment, these lengths are cut with a heated wire. The heated wire deforms the threads at the cut, to thereby lock the outer member 24 onto the threads of the inner member 22 to prevent removal. However, should removal be necessary, the outer member can be carefully counter-rotated off of the threads of the inner member, in which case the threads will typically be restored to a working condition for subsequent re-insertion.

Referring to FIG. 11, in a further embodiment, the cranial flap fixation system of the present invention comprises a three piece design 110. This three piece design generally comprises a bolt 112, a nut 114 and a lock washer 116 for engagement and locking fixation within a burr hole 118 in the cranium 120 of a patient. A driving tool (not shown) can be employed to engage the nut 119 for tightening onto the bolt 112.

As shown in FIG. 11, a presently preferred embodiment of this three piece system shows the bolt 112 having a head portion 126 and a threaded shaft 115. The shaft is of a sufficient length to extend through the thickness of the cranial bone 120 and engage the nut 114 and lock washer 116, and still further to provide sufficient length for easy manipulation of the bolt 112 by the surgeon. It is desired that the head portion 126 of the bolt be considerably wider than the burr hole 118, and preferably about 1.5 to 2 times the diameter of the burr hole for safe and secure placement of the bone flap.

The nut 114 is of a generally cylindrical shape having a top portion 119 and a bottom portion 121 with a threaded aperture 113 extending therethrough for accommodating the threaded shaft 115 of the bolt 112. The bottom portion 121 of the nut 114 is generally cylindrical in shape and is of sufficient length to extend substantially into the burr hole. In the preferred embodiment of this three piece design, the anterior surface of the top portion 119 of the nut 114 includes a semi-rounded surface; however, this anterior surface of the top portion 119 of the nut 114 may be formed to have other shapes or textures. Similarly, in the preferred embodiment the posterior surface 130 of the top portion 119 of the bolt 114 includes a downwardly tapering surface that connects to the bottom portion 121 of the nut 114 to create a bevel.

Figure 12:
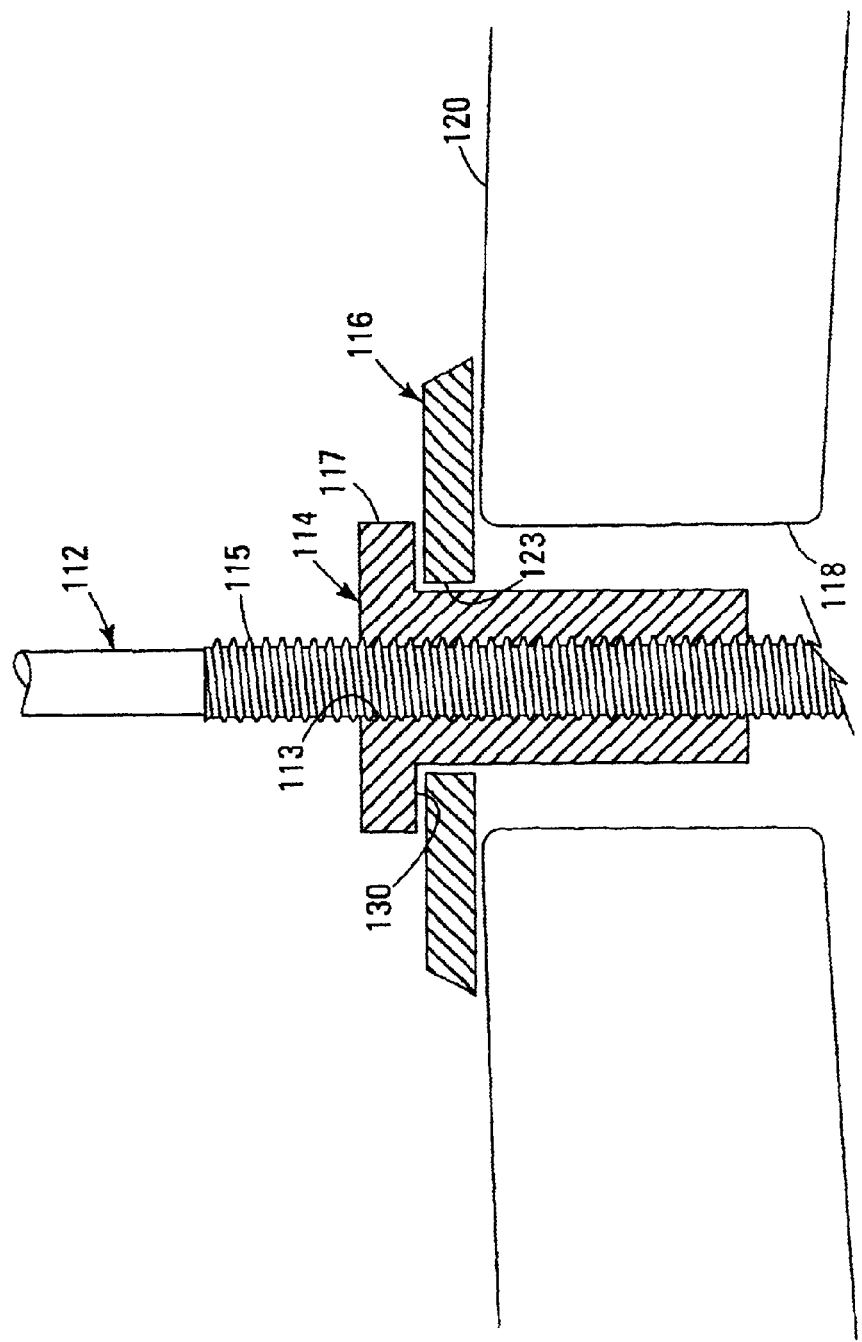
FIG. 12 is a cross-sectional view of another construction of the three piece embodiment of the cranial flap fixation device of the present invention.
Figure 13:
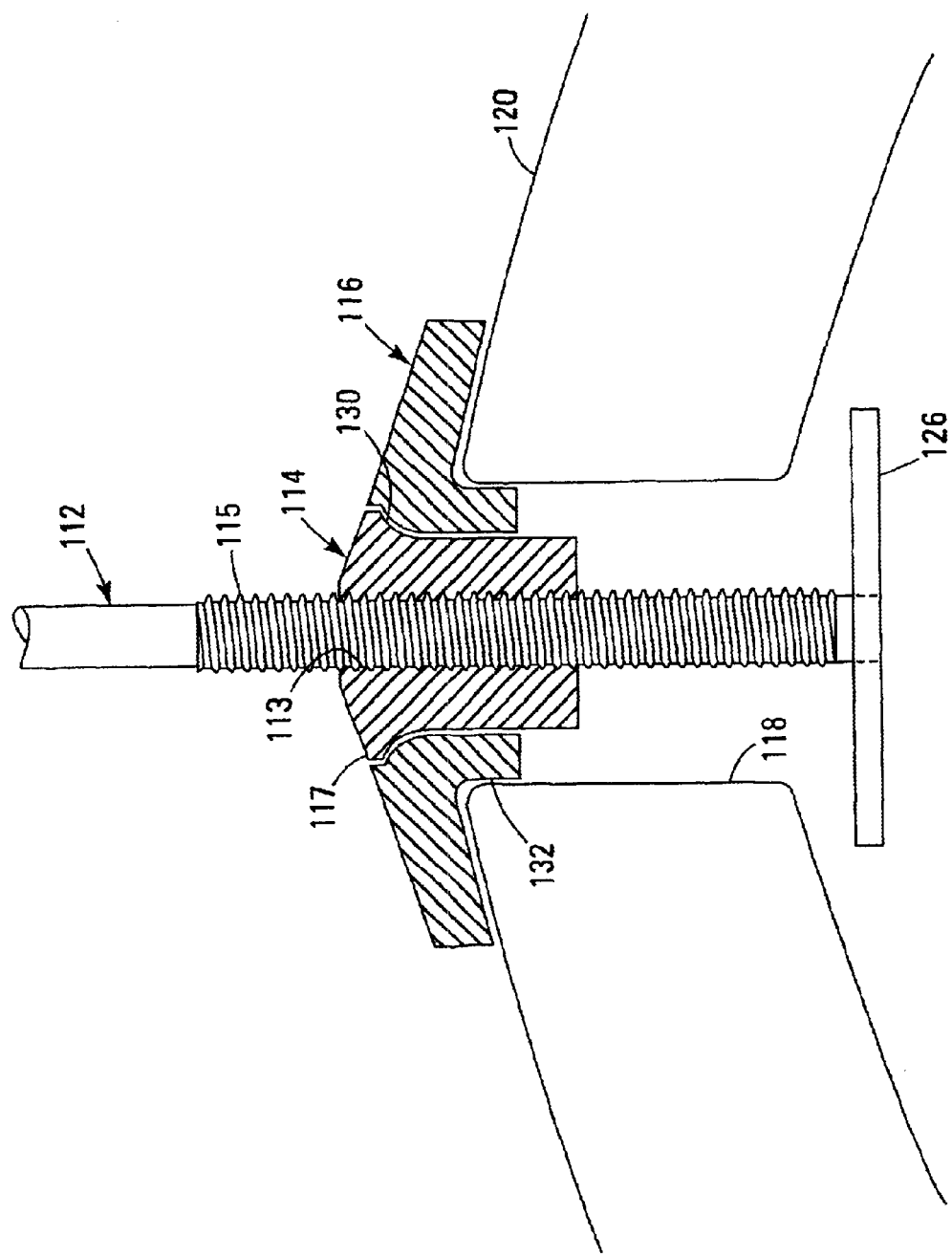
FIG. 13 is a cross-sectional view of a further construction of the three piece embodiment of the cranial flap fixation device of the present invention.

As shown in FIGS. 11–14, the shape of the posterior surface 130 of the nut 114 can take on a variety of configurations so as to achieve a desired or optimal contact with the lock washer 116. In certain embodiments a downwardly extending shoulder 117 is disposed between the anterior surface of the top portion 119 of the nut 114 and the posterior surface 130 of the top portion 119 of the nut 114, as shown in FIGS. 11–13. In the embodiments of FIGS. 12 and 13, for example, the shoulders 117 can be constructed to be substantially parallel with a rotational axis of the threaded shaft 115. In modified embodiments, however, the shoulder 117 may form a more tapered angle. In the configuration shown in FIG. 14, the anterior surface of the top portion 119 of the nut 114 comprises a semi-rounded surface transitioning to the anterior surface of the top portion 119 of the nut 114. In the configuration of FIG. 12, each of the angles connecting the shoulder 117 to the anterior and posterior surfaces of the top portion 118 of the nut 114 generally form right angles.

In the illustrated embodiments, the diameter of the top portion 119 of the nut 114 does not extend beyond the edges of the burr hole. In fact, the preferred embodiment of the nut is such that the nut is substantially the same size or smaller than the burr hole. Alternative embodiments, however, are also possible.

As shown for example in FIG. 11, the lock washer 116 of the present invention includes a generally circular face 131 and a bottom collar portion 132 that is considerably smaller in diameter than the top surface and a nut hole 123 that extends through the lock washer 116. The diameter of the circular face 131 is substantially wider than the diameter of the burr hole 118 and the diameter of the bottom collar portion 132 is of a sufficient width to extend into the burr hole 118 and fit snugly between the nut 114 and the burr hole 118. The diameter of the nut hole 123 is such that the bottom portion 121 of the nut 114 fits snugly therein. The circular face 131 of the lock washer 116 can be configured in a variety of ways, the primary goal of which is to contact and fit snugly against the posterior surface 130 of the nut 114 to friction lock. To that end, in one configuration the circular face 131 may include a beveled top 128 that corresponds to the shoulder 117 and posterior surface 130 of the nut 114 as shown for example in FIG. 11.

In the presently preferred embodiment, the nut 114, imparts a downward force onto a generally radially-inwardly located portion of the lock washer 116, and the edge of the burr hole imparts an upward force onto a radially intermediate portion of the lock washer 116. The downward and upward forces exerted by the nut 114 and the burr hole edge, respectively, can work to place a bind on the lock washer 116 and help to prevent the lock washer 116 and nut 114 from loosening or backing out.

In another configuration the circular face 131 may include a more angular top corresponding in curvature to the shoulder 117 and posterior surface 130 of the nut 114 shown in FIG. 13. In still another configuration, shown in FIG. 12, the lock washer 116 may be configured in a more basic design which lacks the bottom collar portion 132. In such a design, no portion of the lock washer extends into the burr hole. Rather, the lock washer 116 sits between the nut 114 and the surface of the patient's cranium 120 and an aperture 123 extends though the center of the lock washer. The aperture 123 through the lock washer 116 would be of a smaller diameter than the burr hole 118 such that the posterior surface 130 of the nut 114 would frictionally contact the surface of the lock washer 116 closest or near to the aperture 123 when tightened.

In use, the posterior surface 130 of the nut 114 will directly contact the surface of the lock washer 116, placing a first moment arm on the lock washer 116. The edge of the burr hole 118 and the cranium will place a second moment arm on the lock washer 116. These dual moment arms will be somewhat opposed by the structural rigidity of the lock washer 116 to maintain the position of the nut 114 and lock washer 116.

The cranial flap fixation device is preferably provided in sterile packaging, and in one embodiment the bolt 112 is provided in a separate packaging from the nut 114 and lock washer 116. In another embodiment, the nut 114 and lock washer 116 may be provided in a preassembled manner. In yet another embodiment, the nut 114 and lock washer 116 are provided pre-assembled together with a driving tool in a sterile packaging. Due to the fact that the fixation device is intended to remain in the patient's body for an indefinite period of time, the nut 114, bolt 112 and lock washer 116 are preferably formed from resorbable materials wherein the rate of biodegradation is substantially controlled to optimize bone fixation. On the other hand, it may be equally desirable to have the fixation device remain permanently intact within the patient's body in modified embodiments. Such a non-resorbable fixation device may be formed from a variety of materials such as, for example, titanium or non-resorbable plastic.

In practice, the surgeon who is performing the craniotomy procedure can create a bone plate or bone flap by drilling a plurality of burr holes within the cranium. The surgeon will then connect the burr holes using a cutting tool or saw to form a kerf surrounding the bone flap. The bone flap is then removed and the surgical procedure is performed. This procedure may be similar to the procedures described above with reference to FIGS. 7a, 7b, 7c, 8a and 8b. In particular, once the surgeon has completed the procedure and desires to replace and secure the bone flap, the surgeon will select a number of bolts 112, typically representing the same number of burr holes drilled. The surgeon will then hold each bolt 112 by its shaft and, subsequently, the bolts 112 are placed within the burr holes so as to lay near or against the dura of the brain. The bolts 112 may be held in place in a variety of ways such as manually, due to friction of the burr hole in the cranium or by other mechanical positioning means.

Once the bolts 112 have been placed in all of the burr holes, the bone plate or bone flap may be replaced and the nuts 114 and lock washers 116 are then engaged onto the corresponding threaded portions of the bolts 112. The surgeon can then utilize for example a driving tool to tighten the nuts 114 and lock washers 116 so as to secure the bone flap to the cranium. When the surgeon engages for example the driving tool, the downward force of each nut 114 causes a compression of the corresponding lock washer 116. The compressed state of each lock washer 116 biases the lock washer 116 against the nut 114 and cranium 120 so as to utilize friction and opposing forces to minimize movement of the fixation device once the tightening process has been completed. The biased nature of the lock washer 116 may substantially prevent the backward movement of the nut 114 and bolt 112. Once the surgeon has achieved the desired result, the bolt 112 can be cut using a high-temperature wire of a cutting tool so that the bolt is substantially flush with the nut 114.

While this invention has been described with respect to various specific examples and embodiments, it is to be understood that the invention is not limited thereto and that it can be variously practiced within the scope of the disclosure.

What is claimed is:

1. A cranial flap fixation device, comprising:
   a resorbable inner member having a proximal end, a distal end, and a rotational axis extending between the proximal end and the distal end, the resorbable inner member further comprising a head and a threaded shaft extending proximally from the head, the head having a diameter which is greater than a diameter of the threaded shaft and a smooth, bone-contacting surface surrounding the threaded shaft, the surface being substantially free of protrusions extending therefrom;
   a resorbable outer member having a diameter that is greater than the diameter of the threaded shaft, the resorbable outer member further including a threaded aperture for accommodating the threaded shaft of the resorbable inner member therethrough, and a smooth, bone-contacting surface surrounding the threaded aperture, the surface being substantially free of protrusions extending therefrom, the resorbable outer member comprising a plurality of apertures disposed in a pattern on the resorbable outer member; and
   a driving tool constructed to be attached to the resorbable outer member, the driving tool comprising a plurality of protrusions which are disposed on the driving tool in a pattern to facilitate a connection of the plurality of protrusions of the driving tool into the plurality of apertures of the resorbable outer member.

2. The device as set forth in claim 1, wherein the surface of the resorbable inner member that surrounds the threaded shaft is substantially planar.

3. The device as set forth in claim 1, wherein the threaded shaft is threaded on a distal portion substantially adjacent the head of the resorbable inner member, and includes an extended portion proximally disposed relative to the head and having a substantially smooth surface.

4. The device as set forth in claim 1, wherein the resorbable outer member includes a first member and a second member, the first member being structured to provide compressive forces on the second member as the resorbable outer member is tightened against a skull of a patient.

5. The device as set forth in claim 4, wherein the first member includes a top portion, a bottom portion, and a shoulder extending from the top portion, the shoulder being configured to engage with a surface of the second member.

6. The device as set forth in claim 5, wherein the second member includes a beveled top surface configured to engage with the shoulder of the first member.

7. The device as set forth in claim 4, wherein the second member includes a collar portion dimensioned to accommodate a bottom portion of the first member and to be placed within a burr hole in a bone of a patient.

8. The device as set forth in claim 4, wherein the first member of the resorbable outer member is a nut and the second member of the resorbable outer member is a lock washer.

9. The device as set forth in claim 1, wherein the driving tool includes an aperture sized and positioned to accommodate the threaded shaft of the resorbable inner member.

10. The device as set forth in claim 1, wherein the driving tool includes a body surrounding a central aperture dimensioned to receive the threaded shaft of the resorbable inner member, the body having a bottom surface from which the protrusions extend, the bottom surface including a recess extending into the body, the recess being shaped to receive the resorbable outer member such that at least a portion of the resorbable outer member extends into the body of the driving tool.

11. A cranial flap fixation device, comprising:
    a resorbable inner member dimensioned to be placed between a person's skull and brain, and including a head having a diameter, and a shaft extending from the head, the shaft having a diameter less than the diameter of the head and a length wherein a portion of the length is devoid of threads and a portion of the length includes threads; and
    a resorbable outer member dimensioned to be placed over a person's skull, and including a threaded aperture sized to accommodate the threaded portion of the shaft of the resorbable inner member and to permit the portion of the shaft devoid of threads to extend from the resorbable outer member.

12. The device as set forth in claim 11, wherein the portion of the length of the shaft that is devoid of threads includes a smooth surface structured to be gripped by a person's hand.

13. The device as set forth in claim 11, wherein the resorbable outer member includes a plurality of apertures disposed around the threaded aperture, the plurality of apertures being operative to facilitate rotation of the resorbable outer member about the shaft of the resorbable inner member.

14. The device as set forth in claim 13, further comprising a driving tool having a protrusion extending from a surface, the protrusion structured to engage with at least one of the plurality of apertures to facilitate rotation of the resorbable outer member.

15. The device as set forth in claim 14, wherein the driving tool is disposable.

16. The device as set forth in claim 15, wherein the driving tool is prepackaged with one resorbable outer member.

17. The device as set forth in claim 15, wherein the driving tool and the resorbable outer member are prepackaged together in an assembled state.

18. The device as set forth in claim 11, wherein the resorbable outer member comprises a first member and a second member, the first member including a portion surrounded by the second member.

19. The device as set forth in claim 15, wherein the first member includes a body having a smooth outer surface and the threaded aperture of the resorbable outer member extending through the body, and the second member includes a body having an aperture with a smooth inner surface, the aperture of the second member sized to accommodate a portion of to body of the first member.

20. The device as set forth in claim 11, wherein at least one of the resorbable inner member and the resorbable outer member include at least one cell-permeable hole for facilitating bone growth.

21. The device as set forth in claim 11, wherein at least one of the resorbable inner member and the resorbable outer member comprise a copolymer of poly (L,DL) lactate.

22. A cranial flap fixation device, comprising:
    a resorbable inner member dimensioned to be placed between a person's skull and brain, and including a head having a diameter and a threaded shaft extending from the head, the shaft having a diameter less tan the diameter of the head; and
    a resorbable outer member dimensioned to be placed over a person's skull, the resorbable outer member including a first member having an upper portion, a lower portion, and a threaded aperture extending from the upper portion to the lower portion and sized to accommodate the threaded shaft of the resorbable inner member, and a second member dimensioned to accommodate the lower portion of the first member.

23. The device as set forth in claim 22, wherein the threaded shaft includes an extended portion substantially devoid of threads.

24. The device as set forth in claim 22, wherein the first member includes a shoulder extending from the lower portion to the upper portion, the shoulder being located to contact a surface of the second member.

25. The device as set forth in claim 24, wherein the driving tool includes a protrusion operative to be inserted into an aperture provided in the first member of the resorbable outer member.

26. The device as set forth in claim 22, wherein the second member includes an aperture to receive the lower portion of the first member of the resorbable outer member.

27. The device as set forth in claim 22, wherein the threaded shaft of the resorbable inner member is manufactured of a material that can be cut by a high-temperature wire of a cutting tool, and the resorbable outer member is manufactured of a material that retbreads the threaded shaft after the shaft has been cut.

28. The device as set forth in claim 22, further comprising a driving tool structured to fixedly engage with the resorbable outer member to facilitate rotation of the resorbable outer member about the threaded shaft of the resorbable inner member.

29. A cranial flap fixation device, comprising:
a resorbable inner member dimensioned to be placed between a person's skull and brain, and including a head having a diameter and a shaft extending from the head, the shaft having a diameter less than the diameter of the head;
a resorbable outer member dimensioned to be placed over a person's skull, the resorbable outer member including an upper convex surface, a lower concave surface, and an aperture extending from the upper convex surface to the lower concave surface, the aperture being sized to accommodate the shaft of the resorbable inner member therethrough, and the lower concave surface being relatively smooth and devoid of protrusions; and
a driving tool structured to fixedly engage with the resorbable outer member to facilitate rotation of the resorbable outer member about the shaft of the resorbable inner member.

30. The device as set forth in claim 29, wherein the driving tool includes a protrusion operative to be inserted into an aperture provided in the resorbable outer member.

31. A cranial flap fixation device, comprising:
a resorbable inner member dimensioned to be placed between a person's skull and brain. and including a head having a diameter and a shaft extending from the head, the shaft having a diameter less than the diameter of the head; and
a resorbable outer member dimensioned to be placed over a person's skull, the resorbable outer member including an upper convex surface, a lower concave surface, and an aperture extending from the upper convex surface to the lower concave surface, the aperture being sized to accommodate the shaft of the resorbable inner member therethrough, and the lower concave surface being relatively smooth and devoid of protrusions,
wherein the shaft includes a threaded distal portion and a non-threaded proximal portion.

32. The device as set forth in claim 31, wherein the shaft of the resorbable inner member is manufactured of a material that can be cut by a high-temperature wire of a cutting tool, and to resorbable outer member is manufactured of a material that rethreads the threaded shaft after the shaft has been cut.

33. A cranial flap fixation device, comprising:
a resorbable inner member dimensioned to be placed between a person's skull and brain, and including a head having a diameter and a threaded shaft extending from the head, the threaded shaft having a diameter less than the diameter of the head; and
a resorbable outer member dimensioned to be placed over a person's skull, the resorbable outer member including an upper convex surface, a lower concave surface, and a threaded aperture extending from the upper convex surface to the lower concave surface, the threaded aperture being sized to accommodate the treaded shaft of the resorbable inner member therethrough, and the lower concave surface being relatively smooth and devoid of protrusions.

34. The cranial flap fixation device as set forth in claim 33, wherein the lower concave surface is devoid of any threaded collars.

35. The cranial flap fixation device as set forth in claim 33, wherein a thickness of the resorbable outer member near the threaded aperture does not substantially exceed an average thickness of the resorbable outer member.

36. The cranial flap fixation device as set forth in claim 33, wherein a thickness of the resorbable outer member, measured adjacent to the treaded aperture between the upper convex surface and the lower concave surface, is not substantially greater than any other thickness of any portion of the resorbable outer member that is not adjacent to the threaded aperture.

37. The device as set forth in claim 33, further comprising a driving tool structured to fixedly engage with the resorbable outer member to facilitate rotation of the resorbable outer member about the threaded shaft of the resorbable inner member.

38. The device as set forth in claim 37, wherein the driving tool includes a protrusion operative to be inserted into an aperture provided in the first member of the resorbable outer member.

39. The device as set forth in claim 33, wherein the threaded shaft includes an extended portion substantially devoid of threads.

40. The device as set forth in claim 33, wherein the threaded shaft of the resorbable inner member is manufactured of a material that can be cut by a high-temperature wire of a cutting tool, and the resorbable outer member is manufactured of a material that rethreads the threaded shaft after the shaft has been cut.

* * * * *